(12) United States Patent
Re

(10) Patent No.: US 8,292,894 B2
(45) Date of Patent: Oct. 23, 2012

(54) DEVICE FOR ORIENTING THE TIBIAL TUNNEL POSITION DURING AN ACL RECONSTRUCTION

(75) Inventor: Paul Re, Boston, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 808 days.

(21) Appl. No.: 12/367,007

(22) Filed: Feb. 6, 2009

(65) Prior Publication Data

US 2009/0216236 A1   Aug. 27, 2009

Related U.S. Application Data

(60) Provisional application No. 61/066,572, filed on Feb. 21, 2008.

(51) Int. Cl.
  *A61B 17/58* (2006.01)
  *A61B 17/60* (2006.01)
  *A61F 2/00* (2006.01)
(52) U.S. Cl. .............. 606/88; 606/86 R; 606/96
(58) Field of Classification Search .......... 606/87, 606/88

See application file for complete search history.

(56) References Cited

U.S. PATENT DOCUMENTS

| | | |
|---|---|---|
| D245,918 S | 9/1977 | Shen |
| 4,708,139 A | 11/1987 | Dunbar, IV |
| 5,112,337 A | 5/1992 | Paulos et al. |
| 5,139,520 A | 8/1992 | Rosenberg |
| 5,234,434 A | 8/1993 | Goble et al. |
| 5,250,055 A | 10/1993 | Moore et al. |
| 5,409,494 A | 4/1995 | Morgan et al. |
| 5,562,664 A | 10/1996 | Durlacher et al. |
| 5,562,669 A | 10/1996 | McGuire et al. |
| 5,570,706 A | 11/1996 | Howell |
| 5,573,538 A | 11/1996 | Laboureau |
| 5,613,971 A | 3/1997 | Lower et al. |
| 5,743,909 A | 4/1998 | Collette |
| 5,891,150 A | 4/1999 | Chan |
| 5,968,050 A * | 10/1999 | Torrie .................... 606/87 |
| 6,019,767 A | 2/2000 | Howell |
| 6,187,011 B1 | 2/2001 | Torrie |
| 6,254,604 B1 | 7/2001 | Howell |
| 6,254,605 B1 | 7/2001 | Howell |
| 7,458,975 B2 | 12/2008 | May et al. |
| 7,500,990 B2 * | 3/2009 | Whelan ................ 623/13.14 |
| 2003/0009173 A1 | 1/2003 | McGuire et al. |
| 2004/0106928 A1 | 6/2004 | Ek |

(Continued)

FOREIGN PATENT DOCUMENTS

| | | |
|---|---|---|
| CA | 2654486 | 8/2009 |
| FR | 2744621 | 8/1997 |
| WO | WO99/29237 | 6/1999 |
| WO | WO2007/107697 | 9/2007 |

OTHER PUBLICATIONS

PCT International Search Report dated Oct. 19, 2010 for corresponding application PCT/US2010/046764.

(Continued)

*Primary Examiner* — Andrew Yang

(57) ABSTRACT

A device for positioning a tibial tunnel during ACL reconstruction is provided. The device includes a portion insertable into a pre-formed opening in the femur. Also provided is a method for positioning a tibial tunnel during ACL reconstruction. The method includes the steps of forming an opening in a femur bone, inserting a portion of a device into the opening, and using the device to position an opening in a tibia bone.

20 Claims, 11 Drawing Sheets

U.S. PATENT DOCUMENTS

| | | |
|---|---|---|
| 2004/0199166 A1 | 10/2004 | Schmieding et al. |
| 2004/0230302 A1 | 11/2004 | May et al. |
| 2006/0074434 A1 | 4/2006 | Wenstrom, Jr. et al. |
| 2006/0149259 A1 | 7/2006 | May et al. |
| 2006/0149283 A1 | 7/2006 | May et al. |
| 2007/0123902 A1 | 5/2007 | Berberich et al. |
| 2007/0233128 A1 | 10/2007 | Schmieding et al. |
| 2008/0234819 A1 | 9/2008 | Schmieding et al. |
| 2009/0018654 A1 | 1/2009 | Schmieding et al. |
| 2009/0030417 A1 | 1/2009 | Takahashi |
| 2009/0187244 A1 | 7/2009 | Dross |

OTHER PUBLICATIONS

PCT International Search Report dated Oct. 25, 2010 for corresponding application PCT/US2010/046774.

PCT International Search Report dated Oct. 26, 2010 for corresponding application PCT/US2010/046769.

PCT International Search Report dated Oct. 27, 2010 for corresponding application PCT/US2010/046804.

PCT International Search Reports dated Oct. 12, 2010 for the corresponding application PCT/US2010/046351, Oct. 12, 2010 for the corresponding application PCT/US2010/046359, Oct. 19, 2010 for the corresponding application PCT/US2010/046373, and Oct. 26, 2010 for the corresponding application PCT/US2010/046366.

European Search Report for corresponding EP 09250453 date of mailing is May 14, 2009 (4 pages).

European Search Report mailed May 14, 2009 from European Appln. No. 09250453.9 filed Feb. 20, 2009.

* cited by examiner

DEVICE FOR ORIENTING THE TIBIAL TUNNEL POSITION DURING AN ACL RECONSTRUCTION

CROSS REFERENCE TO RELATED APPLICATIONS

This application claims the benefit of and priority to Provisional Application Serial No. 61/066,572 filed Feb. 21, 2008, entitled "GUIDE FOR CREATING A FEMORAL TUNNEL DURING AN ACL RECONSTRUCTION", and incorporates its entire contents by reference herein.

BACKGROUND

1. Technical Field

This invention relates to surgical apparatus and procedures in general, and more particularly to surgical apparatus and procedures for reconstructing a ligament.

2. Background of Related Art

A ligament is a piece of fibrous tissue which connects one bone to another. Ligaments are frequently damaged (e.g., detached or torn or ruptured, etc.) as the result of injury and/or accident. A damaged ligament can cause instability, impede proper motion of a joint and cause pain. Various procedures have been developed to repair or replace a damaged ligament. The specific procedure used depends on the particular ligament which is to be restored and on the extent of the damage.

One ligament which is frequently damaged as the result of injury and/or accident is the anterior cruciate ligament (i.e., the ACL). Looking first at FIGS. 1 and 2, it will be seen that the ACL 5 extends between the top of the tibia 10 and the bottom of the femur 15. A damaged ACL can cause instability of the knee joint and cause substantial pain and arthritis. For this reason, ACL reconstruction is a common procedure with more than 100,000 cases being performed in the United States annually.

Various procedures have been developed to restore and/or reconstruct a damaged ACL through a graft ligament replacement. Traditionally, this procedure is performed utilizing a trans-tibial approach. In this approach, a bone tunnel 20 (FIG. 3) is first drilled up through tibia 10. Tibial tunnel 20 is then used access the interior of the knee joint, and it is from tibial tunnel 20 that the position of a femoral tunnel 25 is determined. In this respect, it should be appreciated that the proper positioning of femoral tunnel 25 is important and that numerous guides have been designed to ensure that tibial tunnel 20 is correctly positioned in order to properly position the resulting femoral tunnel 25.

Looking next at FIGS. 4, 5 and 6, simple tibial tunnel positioning guides generally consist of a hooked tip that may be positioned along the ACL footprint on the tibia at a position chosen by the surgeon. Other tibial tunnel positioning guides are more constraining, in order to attempt to obtain a more reliable and reproducible position for the tibial tunnel. As shown in FIG. 7, some other tibial tunnel positioning guides reference the tibial base of the posterior cruciate ligament ("PCL") (U.S. Pat. No. 5,409,494 to Morgan et al.).

Looking next at FIG. 8, still another guide references the roof of the intercondylar notch, as well as orienting the guide's position relative to the plane of the tibial plateau (U.S. Pat. No. 6,254,605, by Howell et al.). This referencing is done in an attempt to avoid impingement of the femoral roof by the graft ligament.

All of these prior art tibial tunnel positioning guides, while utilizing different referencing points and methods, still share the same overall approach: each of these guides is used to orient the tibial tunnel first, but in a position deemed appropriate for the femoral tunnel, which is thereafter drilled through that tibial tunnel. The limitations of such an approach is that the position of the tibial tunnel is often compromised in order to later drill an appropriate femoral tunnel. This often results in the tibial tunnel being placed in a position which is more posterior and more vertical than is anatomically desired.

Proper placement of the femoral tunnel is imperative in order for the ACL graft to be properly positioned on the femur. However, as a result of using the aforementioned trans-tibial technique, the position of the femoral tunnel is effectively dictated by the position of the first-drilled tibial tunnel. This often results in a femoral tunnel position, and thus, an ACL reconstruction (i.e., graft orientation, etc.) that is less than optimal.

In an attempt to better position the femoral tunnel, surgeons have recently begun utilizing the so-called "medial portal technique" to drill and create the femoral tunnel. An embodiment of a femoral drill guide for use in medial portal techniques is described in commonly owned patent application Ser. No. 12/366,967 entitled "GUIDE FOR CREATING FEMORAL TUNNEL DURING ACL RECONSTRUCTION" filed concurrently herewith, which is based on U.S. Provisional Application No. 61/066,575 filed Feb. 21, 2008, the contents of which are incorporated by reference in its entirety, and is shown generally as femoral guide 100 in FIG. 4. By drilling the femoral tunnel through the medial portal or an accessory portal, the femoral and tibial tunnels may be drilled independently of one another and, therefore, in a more appropriate anatomical position. While the medial portal approach greatly improves the ability of the surgeon to more accurately position the femoral tunnel, the older, simple trans-tibial guides are still used by the surgeon to position the tibial tunnel.

Therefore, it would be beneficial to have a device and method for orienting the position of a second-drilled tibial tunnel based on a first-drilled femoral tunnel. It would further be beneficial to have a device and method for positioning a tibial tunnel utilizing the medial portal approach prior to drilling a femoral tunnel.

SUMMARY

A device for positioning a tibial tunnel during ACL reconstruction is provided. The device includes a portion insertable into a pre-formed opening in the femur. The device may further include an elongated body having proximal and distal ends and an arm extending at an angle from the distal end of the elongated body, the arm being configured for insertion through a medial portal. The portion insertable into a pre-formed opening in the femur may include a tip formed on a distal end of the arm.

The elongated body of the positioning device may be arced. The arm may be configured to point to the position of the resulting tibial tunnel on a tibial plateau when the distal tip is disposed in a femoral tunnel. The arm may include a pointed elbow configured to point to the position of the resulting tibial tunnel on the tibial plateau/ACL footprint. The arm may be configured to orient the angle of the resulting graft in the sagittal plane. The arm may extend from elongated body at an angle from about fifty degrees (50°) to about sixty degrees (60°). The angle between the elongated body and the arm may be adjustable. The arm may include a lateral projection. The proximal end of the elongated body may be configured for connection to an outrigger. The outrigger may be configured to direct a guide wire through the tibial.

Also provided is a method for positioning a tibial tunnel during ACL reconstruction. The method includes the steps of forming an opening in a femur bone, inserting a portion of a device into the opening, and using the device to position an opening in a tibia bone. The step of creating an opening in a femur bone may performed using a medial portal approach. The device may include an elongated body, an arm extending at an angle from a distal end of the elongated body, and a tip formed on a distal end of the arm, the tip being configured for insertion into the femoral tunnel. The method may further include the step of positioning the device by referencing at least one of a lateral wall of the femoral notch and one or more tibial spines.

The device may further include a lateral projection for referencing the femoral notch. The method may further include the step of adjusting the coronal medial/lateral orientation angle of the arm of the device in a way that mimics an intact ACL. The arm of the device may be configured for insertion through a medial portal. The method may further include the step of flexing the knee through a range of motion to check for resultant graft impingement. A proximal end of the arm may include an elbow for engaging the tibia.

Additional provided is a method for positioning a tibial tunnel during ACL reconstruction. The method includes the steps of providing a tibial guide including an elongated body, an arm extending at an angle from a distal end of the elongated body, and a tip formed on a distal end of the arm, the tip including a point for engaging a femur, inserting the distal end of the elongated body into a knee joint using a medial portal approach, engaging the pointed tip with the femur in a position corresponding to that of a desired femoral tunnel, and positioning the tibial guide by referencing at least one of a lateral wall of the femoral notch and one or more tibial spines.

DETAILED DESCRIPTION OF THE EMBODIMENTS

Figure 1:
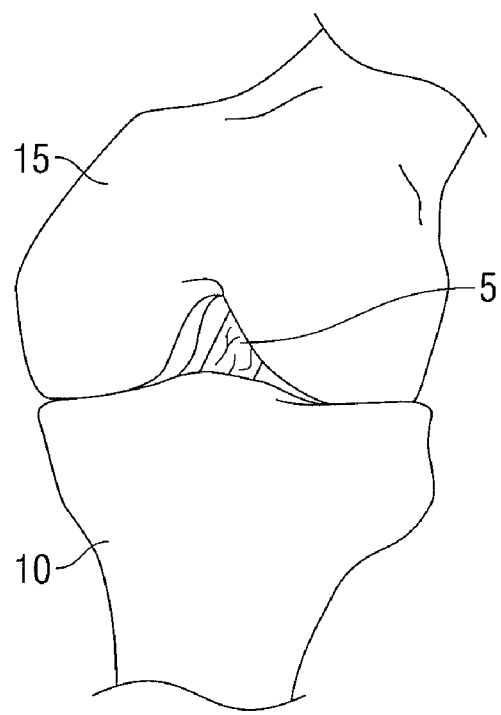
FIG. 1 is a perspective view of a knee joint showing an ACL.
Figure 2:
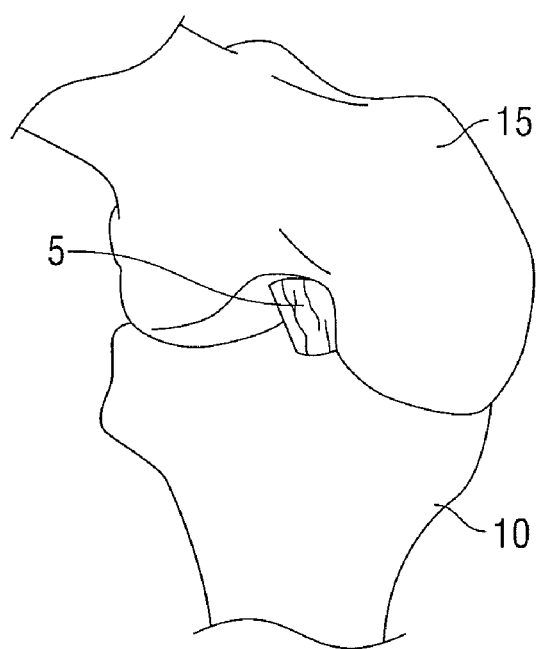
FIG. 2 is an alternate perspective view of the knee joint of FIG. 1.
Figure 3:
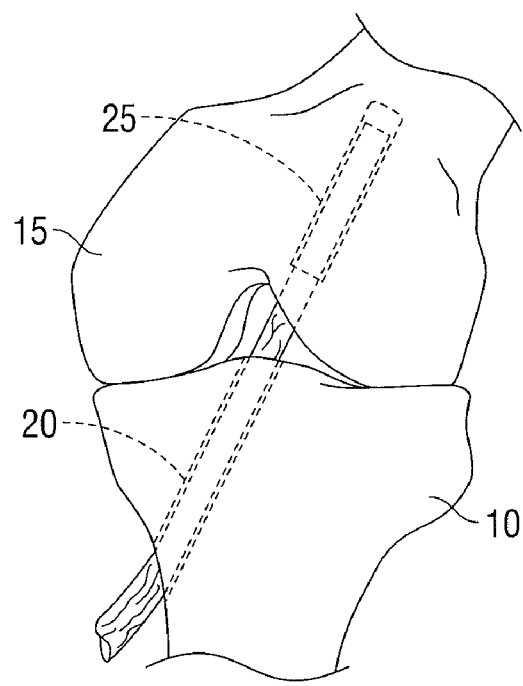
FIG. 3 is a perspective view of a knee joint including tibial and femoral tunnels (shown in phantom) and a ligament graft.
Figure 4:
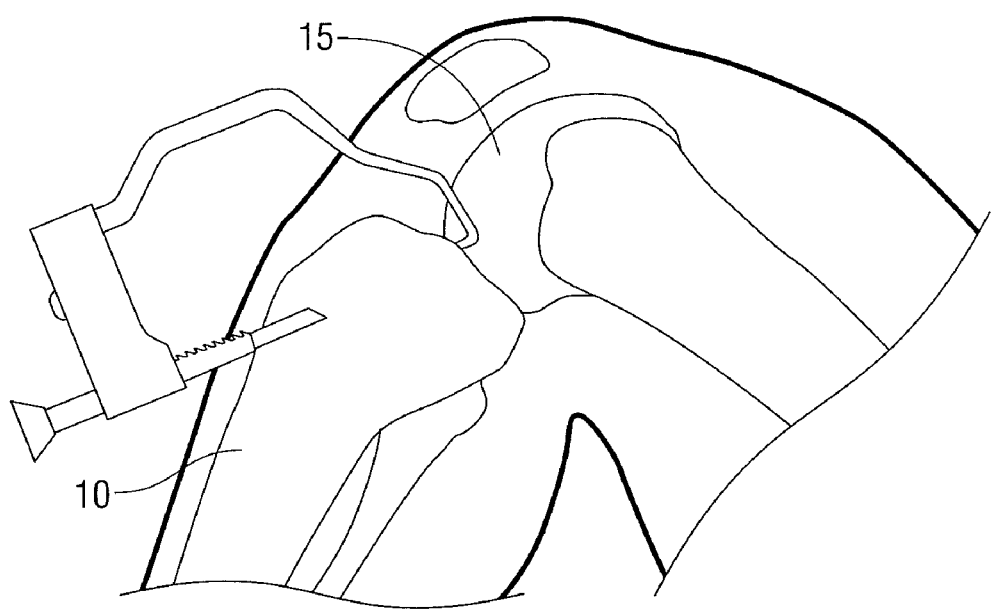
FIGS. 4-8 are views of various prior art embodiments of tibial tunnel positioning guides.
Figure 5:
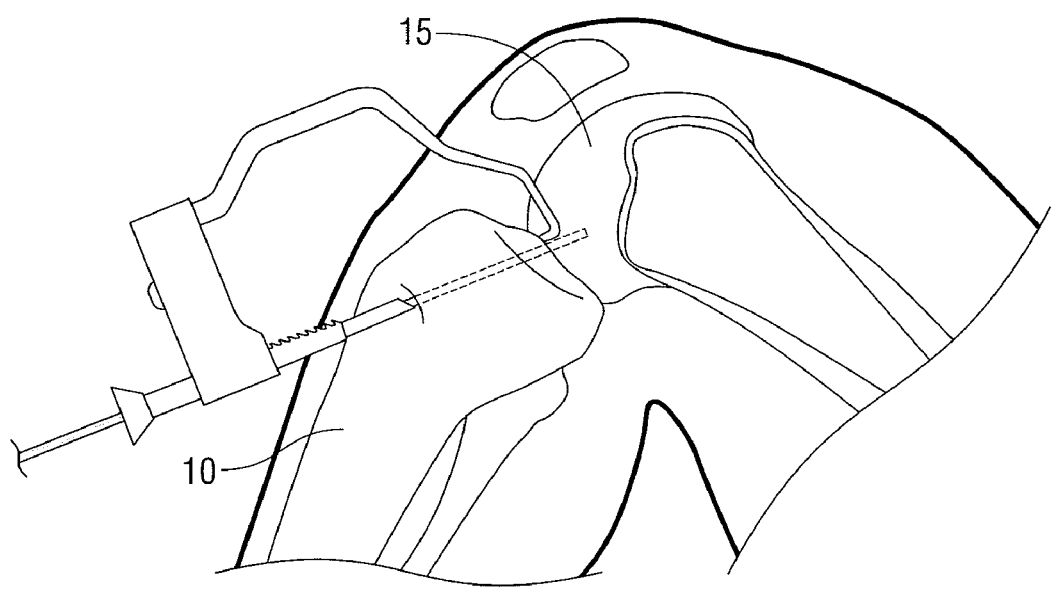
Figure 6:
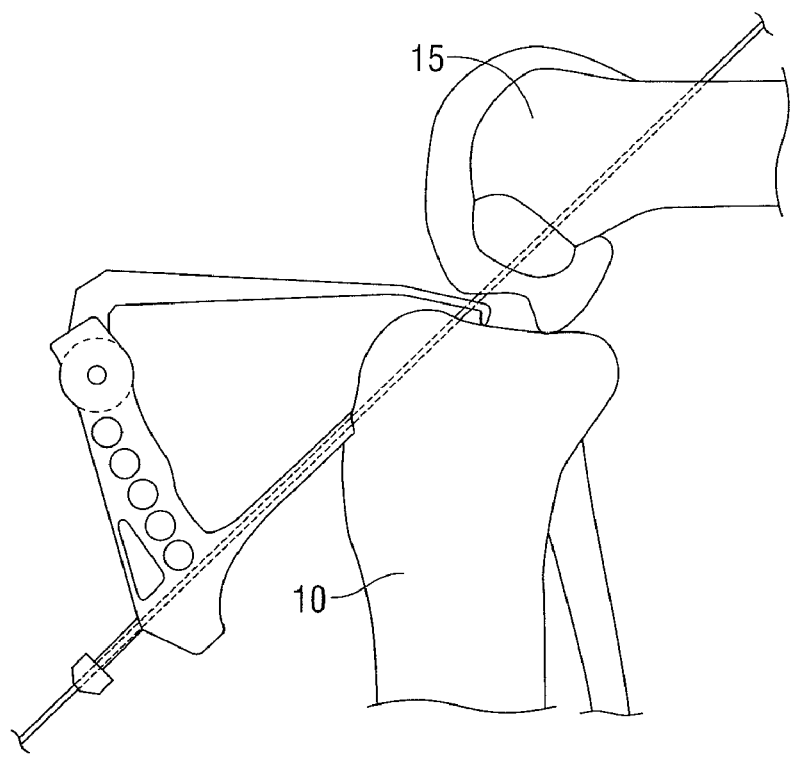
Figure 7:
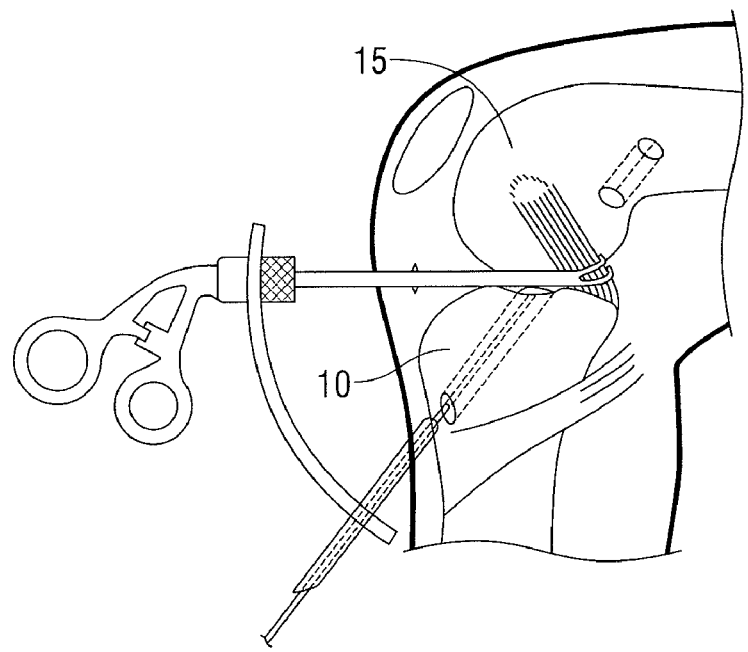
Figure 8:
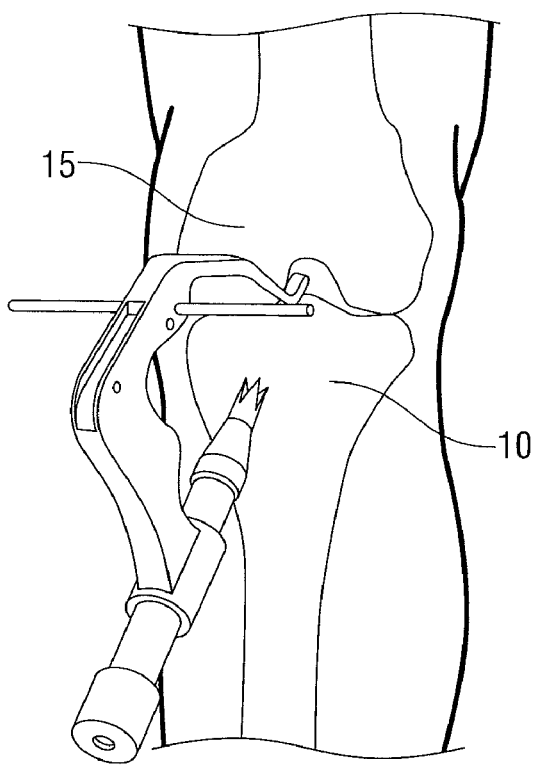
Figure 9:
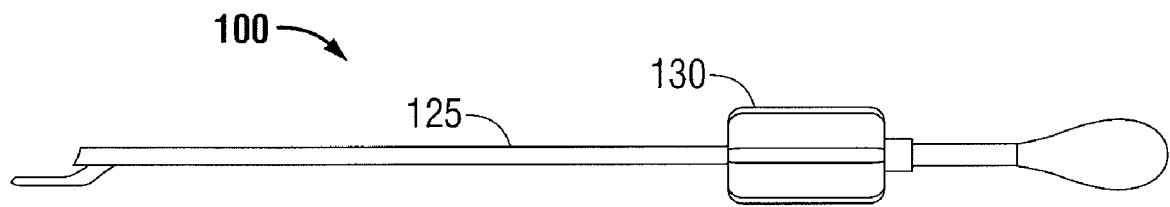
FIG. 9 is a femoral guide for use in ACL reconstruction utilizing the medial portal approach.
Figure 10:
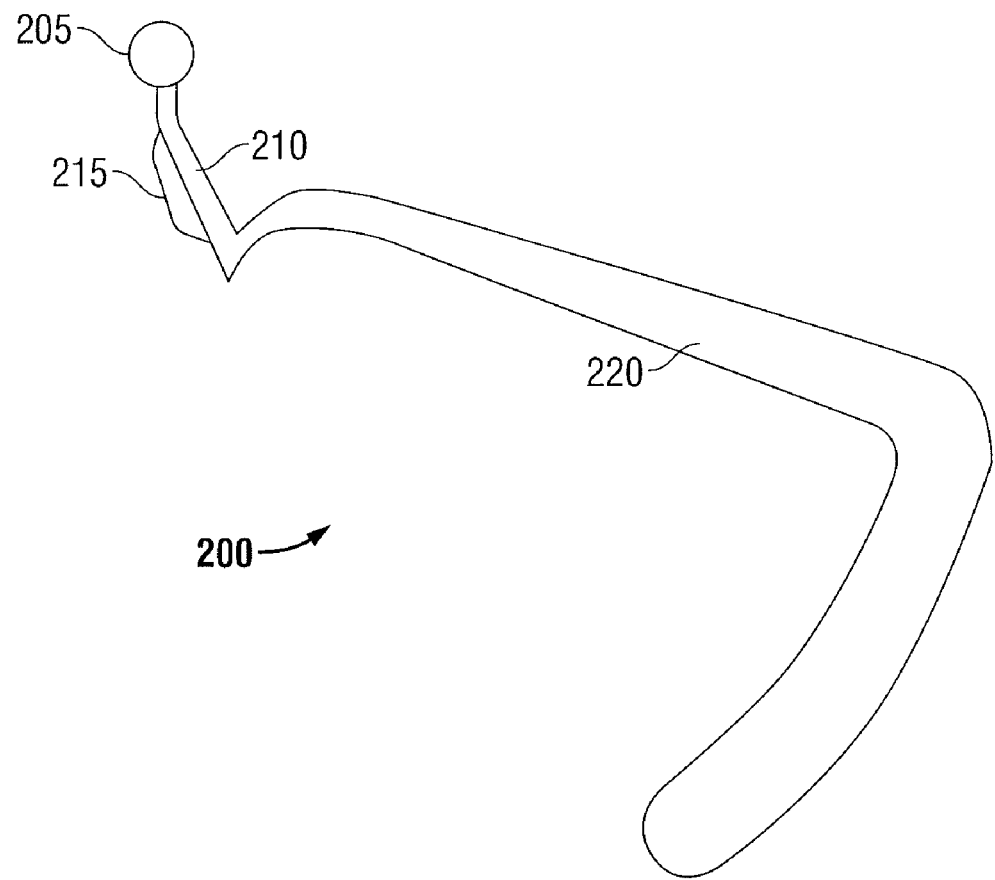
FIG. 10 is a side view of a tibial tunnel positioning guide according to an embodiment of the present disclosure.
Figure 11:
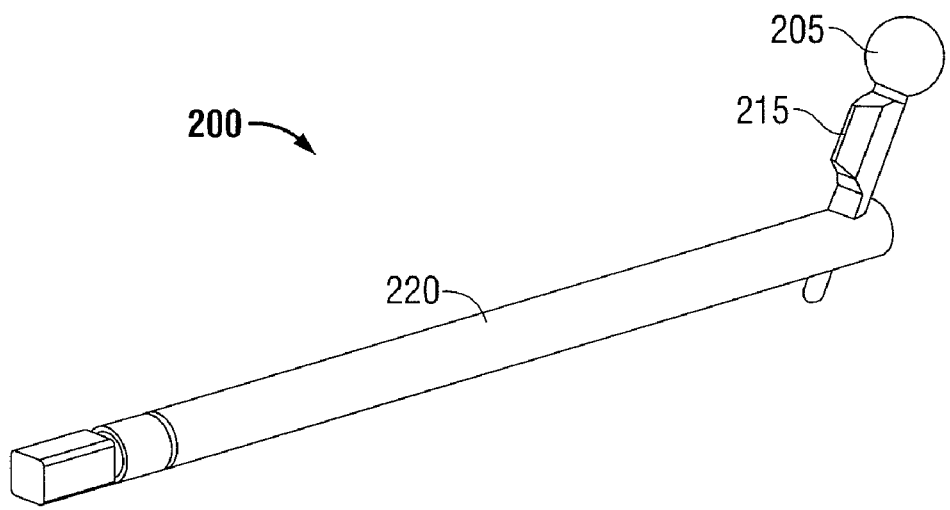
FIG. 11 is a perspective view of a tibial tunnel positioning guide according to an alternative embodiment of the present disclosure.
Figure 12:
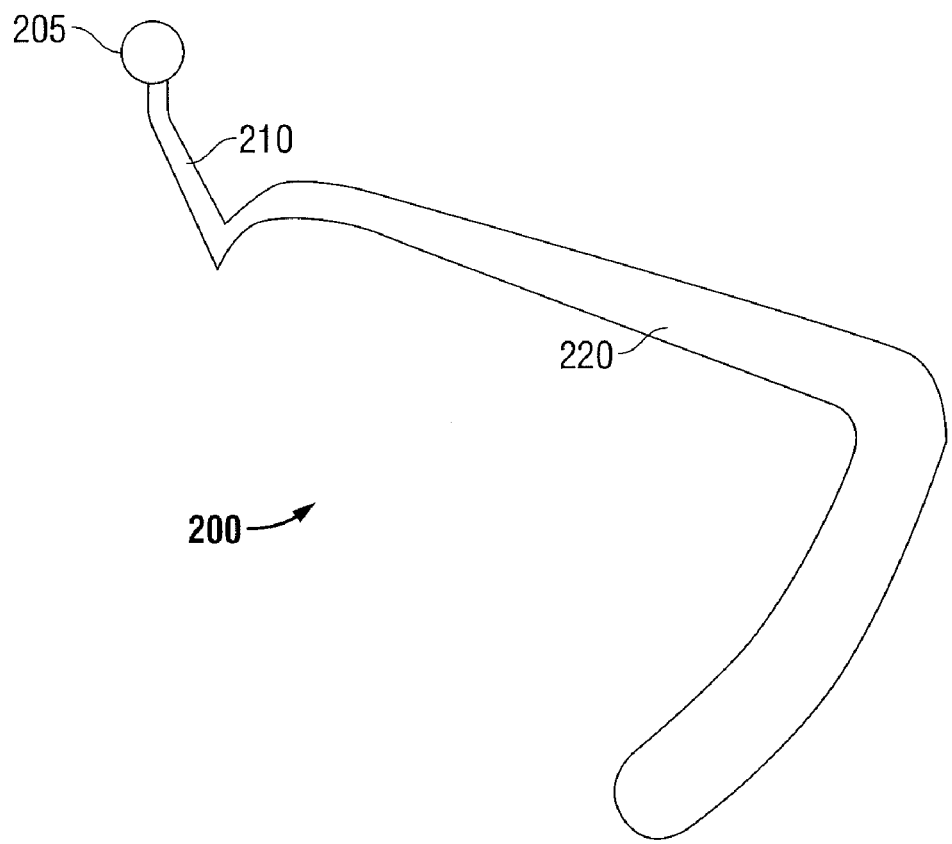
FIG. 12 is a side view of a tibial tunnel positioning guide according to another embodiment of the present disclosure.
Figure 13:
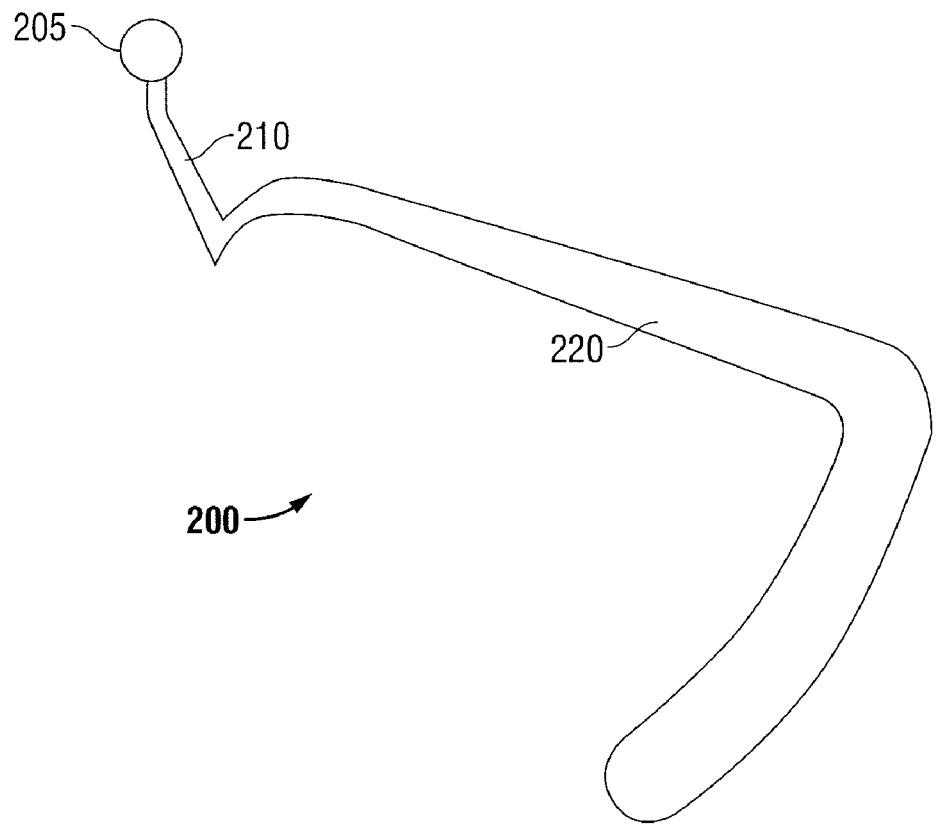
FIG. 13 is a side view of a tibial tunnel positioning guide according to yet another embodiment of the present disclosure.
Figure 14:
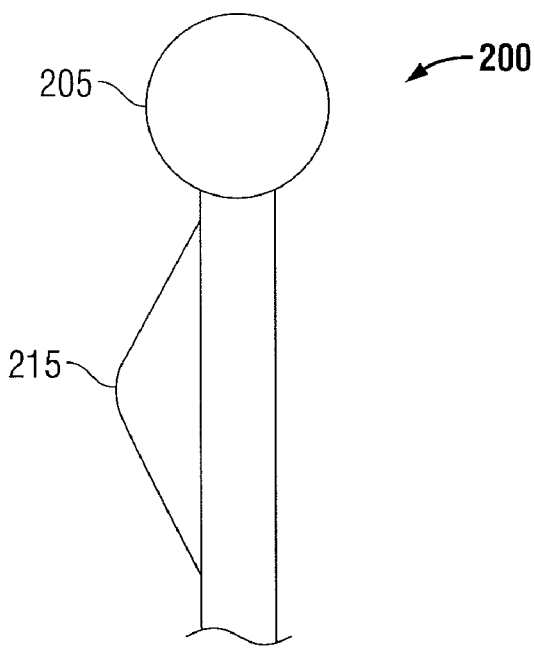
FIG. 14 is an enlarged side view of the distal end of the tibial tunnel positioning guide of FIG. 10.
Figure 15:
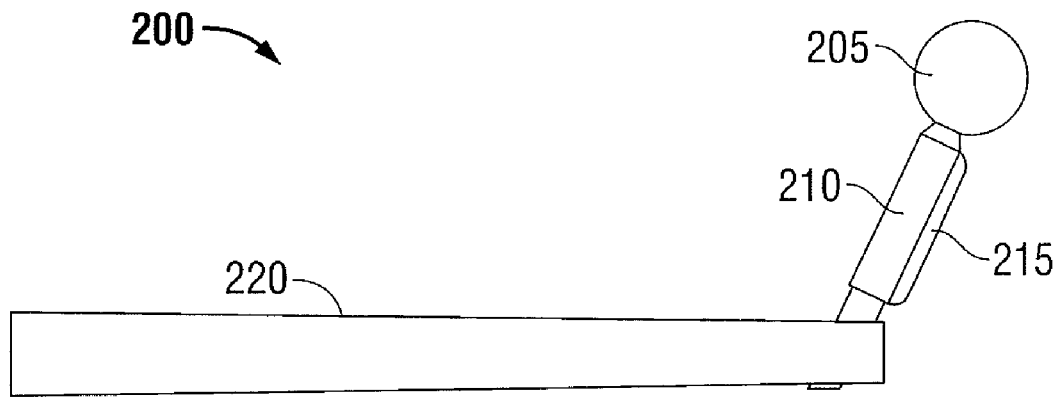
FIG. 15 is a side view of the distal end of the tibial tunnel positioning guide of FIG. 11.
Figure 16:
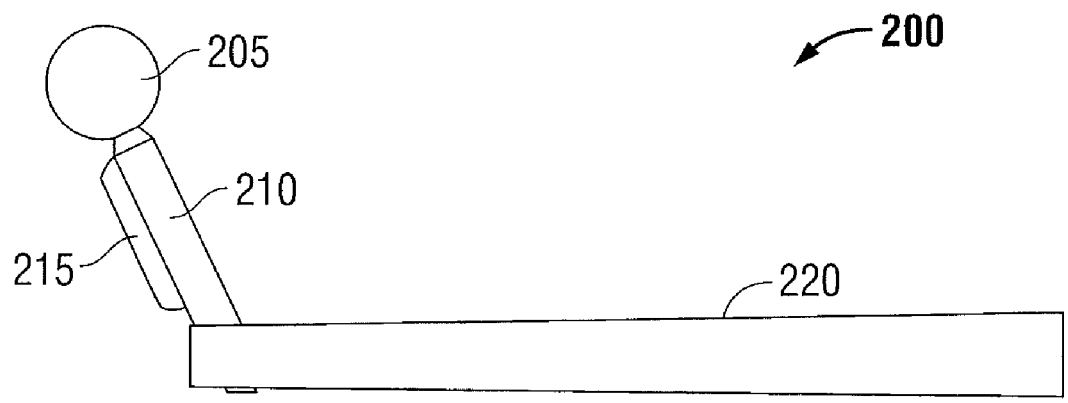
FIG. 16 is an alternate side view of the distal end of the tibial tunnel positioning guide of FIGS. 11 and 15.
Figure 17:
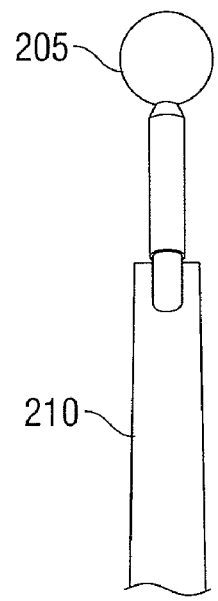
FIG. 17 is an end view of the distal end of the tibial tunnel positioning guide of FIGS. 11, 15 and 16.

Looking now at FIGS. 10-17, there is shown a tibial tunnel positioning guide 200. Tibial tunnel positioning device 200 generally includes a distal tip 205, an arm 210 and an arced body 220. Distal tip 205 is configured to reference a previously-drilled femoral tunnel (e.g., a femoral tunnel drilled using a medial portal approach). Distal tip 205 may be configured in any shape or size suitable to mate with the femoral tunnel. As shown, distal tip 205 is generally ball-tipped and includes a diameter of substantially the size of the previously-drilled femoral tunnel.

Arm 210 extends proximally from distal tip 205 and connects distal tip 205 to arced body 220. Arm 210 is configured to point to the position of the resulting tibial tunnel on the tibial plateau when distal tip 205 is disposed in femoral tunnel 25. Arm 210 is further configured to orient the angle of the resulting graft in the sagittal plane. Studies have determined that, on average, an intact ACL exists in the sagittal plane at an angle of fifty-five degrees (55°) in reference to the perpendicular axis of the tibia (or the plane of the medial or lateral surface of the tibial plateau/joint surface). Accordingly, arm 210 is configured to connect distal tip 205 to body 220 at a pre-determined angle. Arm 210 may be configured to extend from body 220 at any predetermined angle, preferably from about fifty degrees (50°) to about sixty degrees (60°). This configuration allows a surgeon to choose a particularly-angled tibial tunnel positioning guide 200 based on MRI, X-ray or other imaging data. Alternatively, tibial tunnel positioning device 200 may be configured with an angle-adjustable arm (not shown) such that arm 210 may be adjusted to any angle required to meet the needs of the surgeon.

Arm 210 may further include a lateral projection 215. Lateral projection 215 is configured to reference the lateral wall of the femoral notch to help position the resulting tibial tunnel to avoid lateral wall impingement once the graft ligament is positioned. Lateral projection 215 also aids the surgeon in orienting the medial-lateral position of tibial tunnel 20 and its orientation angle in the coronal plane. In this manner, the surgeon may set the coronal medial/lateral orientation angle of the resultant graft position in a way that mimics an intact ACL. Arm 210 may also include a pointed "elbow" which points to the resulting tibial tunnel's guide wire position on the tibial plateau/ACL footprint.

Arced body 220 extends proximally from arm 210 and is configured to facilitate insertion through the medial portal. The configuration of arced body 220 accounts for medial portal positioning to avoid the position of the portal influencing guide placement. More particularly, arm 210 of tibial tunnel positioning guide 200 may be sized and shaped to mirror the size and shape of the ligament graft to be positioned. This allows the surgeon a visual reference of what the resulting graft will look like when placed in the knee. It should be appreciated that forming arm 210 to mirror the form of the ligament graft also allows the surgeon to check for any impingement prior to drilling tibial tunnel 20. For example, once tibial tunnel positioning guide 200 is docked into the pre-drilled femoral tunnel (i.e., by placing the distal ball tip in the femoral tunnel), the surgeon may bring the knee through a range of motion to check for resultant graft impingement before creating the tibial tunnel.

Figure 18:
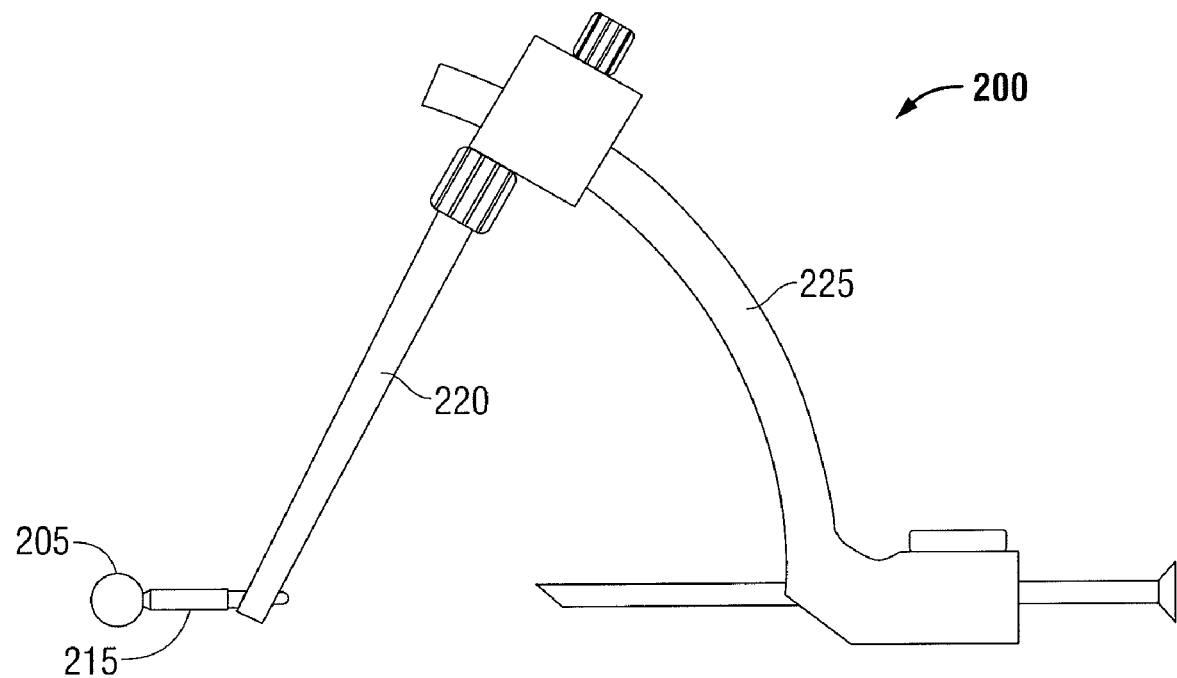
FIG. 18 is a side view of the tibial tunnel positioning guide of FIGS. 11 and 15-17 secured to an outrigger.

Arced body 220 may also be configured for connection to an outrigger 225. (FIG. 18). Outrigger 225 positions the guide wire to be drilled through starting point of the outer tibial cortex. Arced body 220 and outrigger 225 may join at a set angle, or an adjustable angle such that the resultant outer tibial cortex starting point is not positioned too far medially, and in the position desired by the surgeon. In other words, body 220 and/or arm 210 (and therefore distal tip 205) may be set off-angle or off-axis from outrigger 225 if desired.

Figure 19:
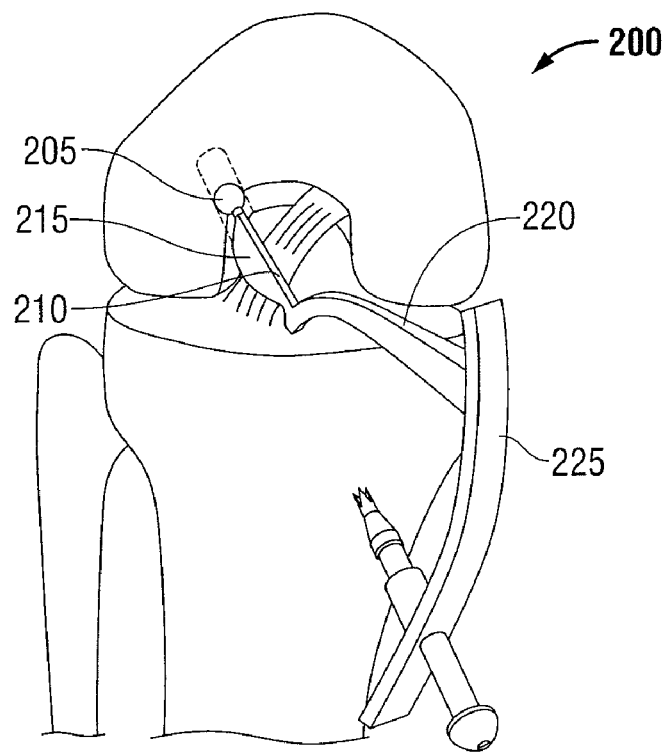
FIG. 19 is partial cut away view of a knee joint including a tibial tunnel positioning guide and outrigger of FIG. 18 positioning.
Figure 20:
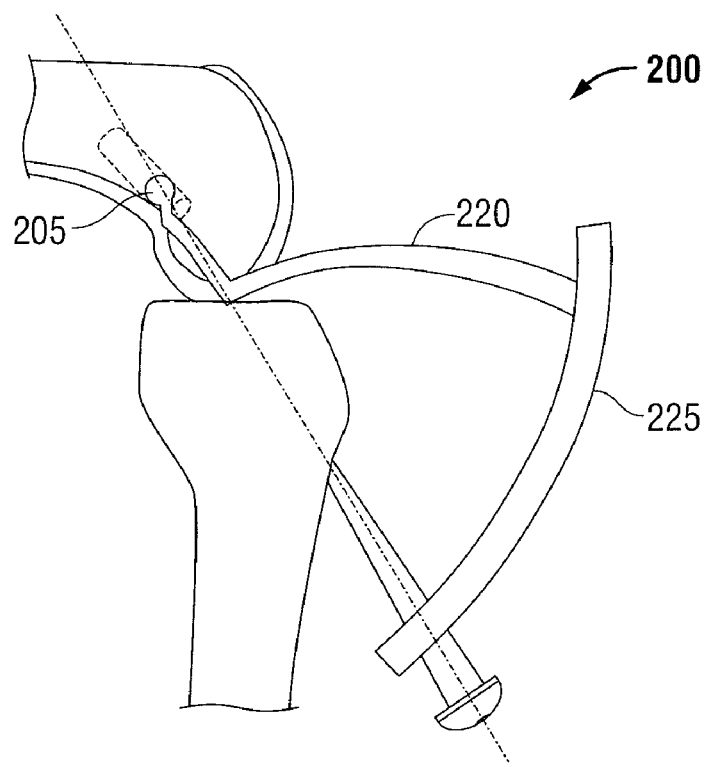
FIG. 20 is a partial cut-away side view of the knee joint of FIG. 19 illustrating the path of a guide wire through the tibia.
Figure 21:
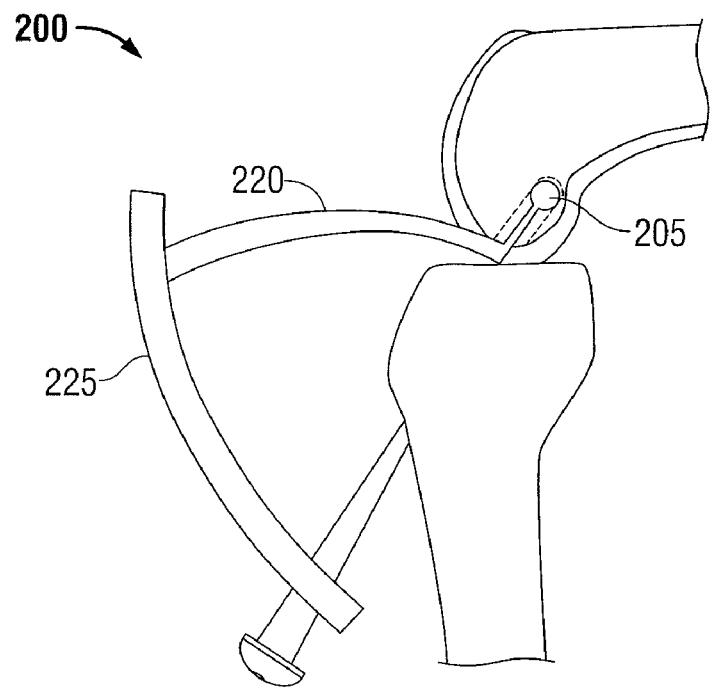
FIG. 21 is an alternate partial cut-away side view of the knee joint of FIGS. 19 and 20.

Looking next at FIGS. 19-21, tibial tunnel positioning guide 200 is placed through a medial portal with distal ball tip 205 of tibial tunnel positioning guide 200 positioned in the pre-drilled femoral tunnel. The anterior/posterior position of the resulting tibial tunnel is determined by selecting the angle of tibial tunnel positioning guide 200. The surgeon may do this in one of two ways: (i) by selecting an appropriately pre-angled guide, or (ii) by setting a desired angle on an angle-adjustable guide. The medial/lateral position of the guide (and therefore the resulting tibial tunnel) is determined by the lateral projection referencing the lateral wall of the notch. In addition, pointed elbow of arm 210 may also reference the tibial spines. In particular, the pointed elbow or arm 210 may reference the medial tibial spine to set the resultant graft in the proper anatomic coronal orientation.

Lastly, with an outrigger attached to tibial tunnel positioning guide 200, the surgeon may move the starting point of the tibial tunnel on the outer cortex, (e.g., medially and away from the MCL), if desired. With the aforementioned positions and references set, tibial tunnel positioning guide 200 is now in place so that the surgeon can confidently drill the tibial tunnel.

Figure 22:
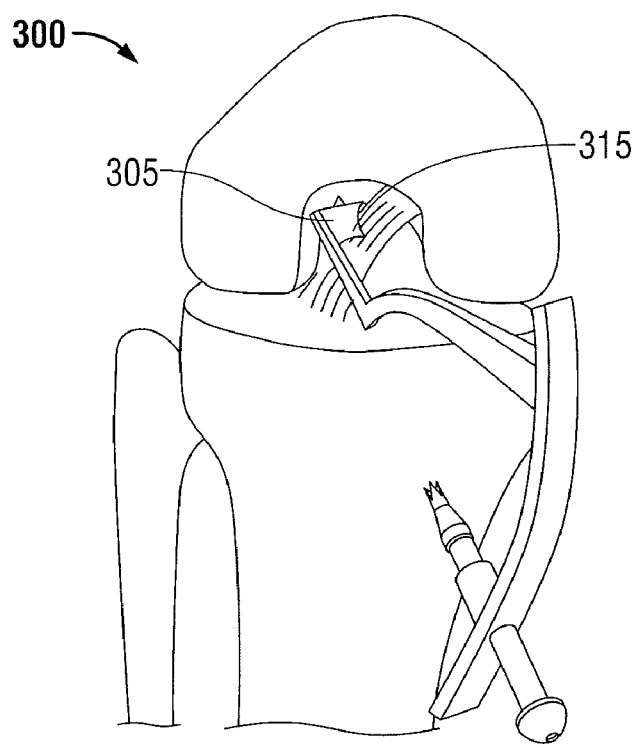
FIG. 22 is a perspective view of a knee joint including a tibial tunnel positioning guide according to still yet another embodiment of the present disclosure and further including an outrigger.

Looking now at FIG. 22, tibial tunnel positioning guide 300 may also be used in an approach where the femoral tunnel has not yet been drilled. In this embodiment, distal tip 305 is configured with a sharp point rather than a ball-tipped end, and a medial projection 315 rather than a lateral projection. The point of distal tip 305 and medial projection 315 are positioned referencing the location of where the PCL is inserted on the femoral notch. Tibial tunnel positioning guide may also be positioned with the point placed at any other spot along the femoral notch, or other position according to the preferences of the surgeon.

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A device for positioning a tibial tunnel during ACL reconstruction, the device comprising:
    an elongated body having proximal and distal ends; and
    an arm extending at an angle from the distal end of the elongated body, wherein the arm is configured for insertion through a medial portal, a distal end of the arm including a tip in the shape of a sphere configured for insertion into a pre-drilled tunnel in a femur.

2. The device of claim 1, wherein the elongated body is arced.

3. The device of claim 1, wherein the arm is configured to point to the desired position of the tibial tunnel on a tibial plateau when the tip is disposed in the femoral tunnel.

4. The device of claim 1, wherein the arm includes a pointed elbow configured to point to the position of a desired location of the tibial tunnel on a tibial plateau/ACL footprint.

5. The device of claim 1, wherein the arm is configured to orient the angle of the resulting graft in the sagittal plane.

6. The device of claim 1, wherein the arm extends from the elongated body at an angle from about fifty degrees (50°) to about sixty degrees (60°).

7. The device of claim 1, wherein the angle between the elongated body and the arm is adjustable.

8. The device of claim 1, wherein the arm includes a lateral projection.

9. The device of claim 1, wherein the proximal end of the elongated body is configured for connection to an outrigger.

10. The device of claim 9, wherein the outrigger is configured to direct a guide wire through the tibia.

11. A method for positioning a tibial tunnel during ACL reconstruction, the method comprising the steps of:
    forming an opening in a femur bone using a medical portal approach;
    inserting a distal portion of a tibial tunnel positioning device into the opening formed in the femur; and
    using the tibial tunnel device to position an opening in a tibia bone while the distal portion of the device is received within the opening formed in the femur.

12. The method of claim 11, wherein the step of forming the opening in the femur bone includes drilling a femoral tunnel.

13. The method of claim 12, wherein the device includes an elongated body, an arm extending at an angle from a distal end of the elongated body, and a tip formed on a distal end of the arm, the tip being configured for insertion into the femoral tunnel.

14. The method of claim 11, further including the step of positioning the device by referencing at least one of a lateral wall of the femoral notch and one or more tibial spines.

15. The method of claim 14, wherein the device further includes a lateral projection for referencing the femoral notch.

16. The method of claim 13, further including the step of adjusting the coronal medial/lateral orientation angle of the arm of the tibial tunnel positioning device in a way that mimics an intact ACL.

17. The method of claim 13, wherein the arm of the device is configured for insertion through a medial portal.

18. The method of claim 11, further including the step of flexing the knee through a range of motion to check for resultant graft impingement.

19. The method of claim 13, wherein a proximal end of the arm includes an elbow for engaging the tibia.

20. A method for positioning a tibial tunnel during ACL reconstruction, the method comprising the steps of:
    providing a tibial guide including an elongated body, an arm extending at an angle from a distal end of the elongated body, and a tip formed on a distal end of the arm, the tip including a point for engaging a femur;
    inserting the distal end of the elongated body of the tibial guide into a knee joint using a medial portal approach;
    engaging the pointed tip of the tibial guide with the femur in a position corresponding to that of a desired femoral tunnel; and
    positioning the tibial guide by referencing at least one of a lateral wall of the femoral notch and one or more tibial spines while the pointed tip of the tibial guide is ingaged with the femur.

* * * * *